US012193993B2

(12) United States Patent
Jain et al.

(10) Patent No.: US 12,193,993 B2
(45) Date of Patent: Jan. 14, 2025

(54) PROCESS FOR PREPARING FILLED HARD-SHELL CAPSULES WITH CELLULOSE OR STARCH-BASED COATINGS WITH A CAPSULE-FILLING MACHINE

(71) Applicant: Evonik Operations GmbH, Essen (DE)

(72) Inventors: Vinay Jain, Mumbai (IN); Ashish Guha, Mumbai (IN); Shraddha Joshi, Thane (IN); Felix Hofmann, Darmstadt (DE); Bettina Hölzer, Bensheim (DE); Hans Bär, Michelstadt (DE)

(73) Assignee: Evonik Operations GmbH, Essen (DE)

( * ) Notice: Subject to any disclaimer, the term of this patent is extended or adjusted under 35 U.S.C. 154(b) by 577 days.

(21) Appl. No.: 17/595,147

(22) PCT Filed: Apr. 30, 2020

(86) PCT No.: PCT/EP2020/061983
§ 371 (c)(1),
(2) Date: Nov. 10, 2021

(87) PCT Pub. No.: WO2020/229192
PCT Pub. Date: Nov. 19, 2020

(65) Prior Publication Data
US 2022/0241155 A1    Aug. 4, 2022

(30) Foreign Application Priority Data

May 15, 2019    (IN)    .............................. 201941019449

(51) Int. Cl.
*A61J 3/07*    (2006.01)
*A23P 10/30*    (2016.01)
*A61K 9/48*    (2006.01)

(52) U.S. Cl.
CPC ............... *A61J 3/074* (2013.01); *A23P 10/30* (2016.08); *A61K 9/4891* (2013.01)

(58) Field of Classification Search
CPC . A61J 3/074; A61J 3/071; A23P 10/30; A61K 9/4891; A61K 9/4816; A61K 47/10; A61K 47/36; A61K 47/38
See application file for complete search history.

(56) References Cited

U.S. PATENT DOCUMENTS

| | | | |
|---|---|---|---|
| 4,138,013 A | 2/1979 | Okajima | |
| 11,523,992 B2 * | 12/2022 | Jain | A61K 9/4891 |
| 11,904,056 B2 * | 2/2024 | Holzer | A61K 47/26 |
| 11,980,692 B2 * | 5/2024 | Guha | A61K 9/4891 |
| 2004/0069300 A1 | 4/2004 | Roversi | |
| 2014/0079792 A1 * | 3/2014 | Schattka | A61K 9/5026 |
| | | | 514/263.36 |
| 2017/0119681 A1 * | 5/2017 | Bravo Gonzaléz | A61K 9/4891 |
| 2021/0361585 A1 | 11/2021 | Guha et al. | |
| 2022/0142929 A1 | 5/2022 | Hölzer et al. | |
| 2023/0000780 A1 | 1/2023 | Haksar et al. | |

FOREIGN PATENT DOCUMENTS

| | | | |
|---|---|---|---|
| CA | 2769046 | 2/2011 | |
| CN | 102448446 H2 | 5/2012 | |
| JP | S61221117 | 10/1986 | |
| JP | 2003325642 | 11/2003 | |
| WO | 2011/012369 | 2/2011 | |
| WO | WO-2013170012 A2 * | 11/2013 | ........... A61K 31/568 |
| WO | 2015/177028 | 11/2015 | |
| WO | 2019/096833 | 5/2019 | |

OTHER PUBLICATIONS

U.S. Office Action dated Apr. 20, 2022 in U.S. Appl. No. 17/595,145, 11 pages.
U.S. Office Action dated Jul. 6, 2023, in U.S. Appl. No. 17/438,886, 14 pages.
U.S. Appl. No. 17/757,060, filed Jun. 8, 2022.
A.A. Attama, "*Polyelectrolyte Complexes of Eudragit L30 D-55 and Gelatin: Antinociceptive Activity of Entrapped Piroxicam*", Drug Delivery, vol. 14, 2007, pp. 155-162.
Cole, et al., "*Enteric coated HPMC capsules designed to achieve intestinal targeting*", International Journal of Pharmaceutics, vol. 231, 2002, pp. 83-95.
Database WPI, Week 198646, Thomson Scientific, London, GB, AN 1986-300710, XP002799753, corresponding to JPS61221117, 2017, 1 page.
Database WPI, Week 200405, Thomson Scientific, London, GB, AN 2004-47266, XP002799752, corresponding to JP2003325642, 2017, 2 pages.

(Continued)

*Primary Examiner* — Robert A Wax
*Assistant Examiner* — Quanglong N Truong
(74) *Attorney, Agent, or Firm* — Grüneberg and Myers PLLC

(57) ABSTRACT

A process can be used for preparing a polymer coated hard-shell capsule, filled with a fill containing a biologically active ingredient. The hard-shell capsule contains a body and a cap, and in a closed state, the cap overlaps the body in a pre-locked state or a final-locked state. The material of the body and cap contains an ethyl-, methyl-, or propyl-ether of cellulose, starch, or pullulan. The hard-shell capsule is coated with a coating layer, containing one or more anionic cellulose(s), ethyl cellulose, and/or one or more starches comprising at least 35% by weight of amylose, where the coating layer is present in an amount of about 1 to 5.8 mg/cm$^2$. The process involves providing the polymer-coated hard-shell capsule in the pre-locked state to a capsule-filling machine, separating the body and the cap, filling the body with the fill, and rejoining the body and the cap in the final-locked state.

20 Claims, 1 Drawing Sheet

(56) References Cited

OTHER PUBLICATIONS

European Search Report issued Feb. 25, 2020 in European Application No. 19197993.9, 6 pages.
Huyghebaert, et al., "*Alternative method for enteric coating of HPMC capsules resulting in ready-to-use enteric-coated capsules*", European Journal of Pharmaceutical Sciences, vol. 21, XP-002560461, 2004, pp. 617-623.
International Search Report issued Sep. 29, 2020 in PCT/EP2020/061983, 6 pages.
Lu, et al., *Dissolution of Gelatin Capsules: Evidence and Confirmation of Cross-Linking*, Dissolution Technologies, Aug. 2017, 16 pages.
Written Opinion issued Sep. 29, 2020 in PCT/EP2020/061983, 12 pages.
Bär et al., U.S. Appl. No. 18/563,517, filed Nov. 22, 2023.
Bär et al., U.S. Appl. No. 18/563,327, filed Nov. 21, 2023.
U.S. Appl. No. 18/563,517, Bär et al.
U.S. Appl. No. 18/563,327, Bär et al.
U.S. Appl. No. 15/733,083, filed May 13, 2020, 2021/0361585, Guha et al.
U.S. Appl. No. 17/438,886, filed Sep. 13, 2021, Hölzer et al.
U.S. Appl. No. 17/595,145, filed Nov. 10, 2021, Jain et al.
U.S. Office Action dated Jun. 14, 2022, in U.S. Appl. No. 15/733,083, 12 pages.

\* cited by examiner

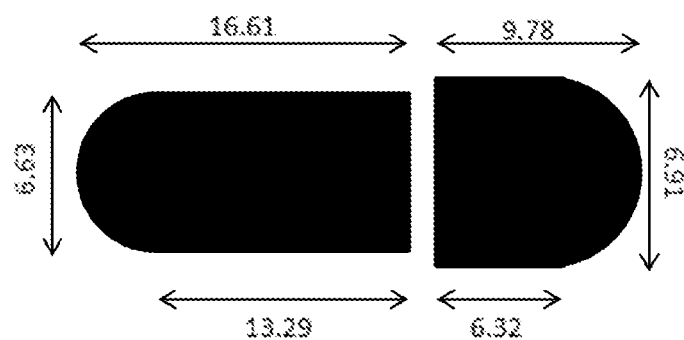

PROCESS FOR PREPARING FILLED HARD-SHELL CAPSULES WITH CELLULOSE OR STARCH-BASED COATINGS WITH A CAPSULE-FILLING MACHINE

CROSS-REFERENCE TO RELATED APPLICATIONS

This application is the National Stage entry under § 371 of International Application No. PCT/EP2020/061983, filed on Apr. 30, 2020, and which claims the benefit of priority to Indian application No. 201941019449, filed on May 15, 2019. The content of each of these applications is hereby incorporated by reference in its entirety.

BACKGROUND OF THE INVENTION

Field of the Invention

The invention is in the field of processes for preparing filled polymer-coated hard-shell capsules with a capsule filling machine.

Description of Related Art

U.S. Pat. No. 4,138,013 describes hard shell capsules with enteric properties. The hard-shell capsules comprise telescopically engaged body and cap portions. The capsule body and cap portions are formed by dip-molding using homogeneous film-forming mixt comprising selected from hydroxypropyl methyl cellulose (HPMC), a mixture of (1) hydroxypropyl methyl cellulose and an ammonium salt of cellulose acetate phthalate or (2) gelatin and an ammonium salt of a copolymer of (meth)acrylic acid and methacrylic acid alkyl ester. The capsules itself have already enteric properties without applying a further enteric coating layer.

Xujin Lu and Pankaj Shah, "Dissolution of Gelatin Capsules: Evidence and Confirmation of Crosslinking" in Dissolution technologies August 2017, 6-20. The authors discuss that cross-linking is a common problem in the dissolution of gelatin capsules, A. A. Atama (2007) "Polyelectrolyte Complexes od Eudragit L30 D-55 and Gelatin. Antinociceptive Activity of Entrapped Piroxicam. The author discuss the interaction of EUDRAGIT® L 30 D-55. EUDRAGIT® L 30 D-55 is a 30% aqueous dispersion of an anionic copolymer based on methacrylic acid and ethyl acrylate. Gelatin type A is generated by acid pretreatment of pig skin. The isoelectric point (IEP) of gelatin is between 7-9. Below pH 8 gelatin A is positively charged and can interact with negatively charged EUDRAGIT® L 30 D-55.

Huyghebaert et al., *European Journal of Pharmaceutical Sciences* 21 (2004) 617-623, describe an alternative method for the enteric coating of capsules made of HPMC in which ready-to-use enteric capsule parts are obtained. It is reported that, in contrast to gelatine capsules, HPMC capsules can be enteric coated relatively easily from aqueous preparations. However, it is necessary to additionally apply a sealing between the capsule halves, e.g. through a gelatine solution to be applied manually, in order to avoid a leakage of the capsule and an uncontrolled escape of the contents in the stomach. Another technique is to apply water/ethanol mixtures between the capsule halves and to weld the parts together at 40-60° C. Using aqueous preparations (EUDRAGIT® FS 30 D, EUDRAGIT® L 30 D-55, Aquoat® AS-HF or Sureteric®) based on (meth)acrylate copolymers or polyvinyl acetate phthalate, plasticizers such as triethyl citrate and further auxiliaries, such as, for example, talc, it is possible to provide HPMC capsules with an enteric film from separately coated bodies and caps. A separate sealing step can be prevented in the case of this coating technology. In particular, HPMC capsules which have been coated with (meth)acrylate copolymers are depicted as particularly advantageous in the sum of their properties.

WO 2011/012369A1 describes a coating composition for the enteric coating of capsule halves made of water-soluble or water-swellable polymer material.

JP2003-325642A describes a hard-shell empty capsule with enteric solubility and a manufacturing method for such a hard-shell empty capsule. The capsule cap is coupled with the capsule body in the semi-locked state and an enteric solubility membrane is formed on the entire surface. Then the capsule cap is removed from the capsule body and the contents are fill-packed. The parts are then coupled in a locked state. This allows to avoid the application of a coating after the filling of the capsule, which would a thermal burden for the contents. Also, a seal sticker sealing of the capsule after filling can be avoided, since there is an overlap of the coating in the locked state, which seals the gap between the capsule cap and capsule body. The capsule may be filled with the desired contents such as propolis, raw royal jelly, black-vinegar extract. The capsules as described are made from gelatin by a dip coating procedure by immersing metallic molds into a gelatin and water dispersion. The metallic molds are pulled up, rotated, cooled and dried. Thereby, cylindrical membranes are formed in uniform thickness, cut in the dimensions as required as a capsule caps or as capsule bodies. Capsule caps and capsule bodies are coupled in a semi-locked state. An enteric soluble substance may be applied by spray coating.

The enteric soluble substance according to JP2003-325642A may be a plant or animal protein originating in wheat, a soybean, a collagen, gelatin, etc., cellulose-acetate phthalate, a cellulose-acetate succinate, cellulose-acetate maleate, hydroxypropyl-methylcellulose phthalate, hydroxypropyl-methylcellulose acetate succinate, polyvinyl-acetate phthalate, polyvinyl butyrate phthalate. The amount of coating is more than the quantity performed by conventional enteric solubility capsule formation, 20 to 80% by weight, 40 to 60% by weight desirable. The film thickness is about 0.1 to about 0.5 mm. These film thicknesses are larger than the tolerance variation of the outer diameter of the capsule body and the internal diameter of the capsule cap.

JP S61-221117A describes an enteric hard capsule formation to be used, for example, in the medical field. The capsules are coated in a pre-locked state before filling to avoid the drawbacks of conventional hard capsules coated with enteric solvent after filling, e.g. losses of expensive medicines. The coating in the pre-locked state result in a part overlapping of the body with cap that has a sufficient bucking effect to prevent gastric juices from entering into the capsule from the fitting part of the cap and the body. The invention uses ordinary gelatin capsules that may be of the so-called locking method of "snap-fit". As enteric solvents hydroxypropyl methyl cellulose phthalate, hydroxypropyl methyl cellulose acetate phthalate, cellulose acetate phthalate and methacrylic acid-methyl methacrylate copolymers may be used. In the examples capsules of size No. 1 were coated with 14 and 38 mg hydroxypropyl methyl cellulose phthalate (HP-55, Shin-Etsu Chemical Co., Ltd). It was found that 18 mg per capsule with a film thickness of around 80 μm was preferable.

Hard-shell capsules which are enteric coated in a pre-locked state, opened, filled with a fill and are then closed to a final-locked state are in principle known from JP2003-325642A and JP S61-221117A. Both citations describe the use of gelatin capsules which tend to cross linking during storage (Xujin Lu and Pankaj Shah, "Dissolution of Gelatin Capsules: Evidence and Confirmation of Crosslinking" in Dissolution technologies August 2017, 6-20). The gelatin capsules are pre-coated with a coating zein (JP2003-325642A) or hydroxypropyl methyl cellulose acetate phthalate (HP-55 JP2003-325642A).

The use of enteric coated capsules in a pre-locked state seems to be advantageous since the application of additional sealing steps as discussed in Huyghebaert et al. (European Journal of Pharmaceutical Sciences 21 (2004) 617-623) can be avoided. Also, a thermal burden for the fill that takes place when the coating is applied after the filling, can be avoided by means of coating in the pre-locked state before capsule filling.

For industrial scale production a high turnover and output process is desirable. Such high turnover and output can be achieved by use of automated capsule-filling machines. Half and fully automated capsule filling machines can process provided capsules which are already coated in the pre-locked state and rapidly perform the steps of separating the body and the cap, filling the body with the fill and rejoining the body and the cap in the final-locked state. A fully automated machine is capable to run at a speed of 1,000 or even a much more higher number of processed capsules per hour. The high speed however causes high mechanical stress to the pre-locked capsules and especially to the mechanical resistance of the coatings. Therefore, there is a need to provide a process, which allows the processing of capsules coated in a pre-locked state in a capsule filling machine without impairing properties such as resistance in acidic medium (less than 10% active ingredient release at pH 1.2 in 120 min) and rapid dissolution at higher pH (pH 5.5 or above, pH 6.8).

SUMMARY OF THE INVENTION

The invention is concerned with a process for preparing a polymer coated hard-shell capsule, filled with a fill comprising a biologically active ingredient, wherein the hard-shell capsule is comprising a body and a cap, wherein in a closed state the cap overlaps the body either in a pre-locked state or in a final-locked state, wherein the material of the body and the cap comprises an ethyl-, methyl- or propyl-ether of cellulose, starch or pullulan, wherein the hard-shell capsule is coated with a coating layer that covers the hard-shell capsule in the pre-locked state, wherein the coating layer is comprising one or more anionic cellulose(s), ethyl cellulose and/or one or more starches comprising at least 35% by weight amylose, wherein the coating layer is present in an amount of about 1 to 5.8 mg/cm$^2$, preferably 2 to 5 mg/cm$^2$, wherein a dried film with a thickness of 250 µm, corresponding to the composition of the coating layer, shows an elongation at break of about 15 to 500, preferably 20 to 250%, wherein the polymer-coated hard-shell capsule is provided in the pre-locked state to a capsule-filling machine, which performs the steps of separating the body and the cap, filling the body with the fill and rejoining the body and the cap in the final-locked state.

BRIEF DESCRIPTION OF THE DRAWING

The FIGURE shows a schematic drawing of the body (left) and the cap (right) of a Vcaps® Plus size 1 hard-shell capsule with the relevant dimensions in mm.

DETAILED DESCRIPTION OF THE INVENTION

Biologically Active Ingredient

The process as disclosed refers to a polymer coated hard-shell capsule, filled with a fill comprising a biologically active ingredient. A biologically active ingredient may be defined as an ingredient that may after delivery or intake confers a preventive or therapeutical effect in an animal or human body. The biologically active ingredient is preferably a pharmaceutically active ingredient and/or a nutraceutically active ingredient.

Pharmaceutically or Nutraceutically Active Ingredients

The invention is preferably useful for immediate, enteric or sustained release formulated pharmaceutical or nutraceutical dosage forms with a fill-in of pharmaceutically or nutraceutically active ingredients.

Suitable therapeutic and chemical classes of pharmaceutically active ingredients which members may be used as fill-in for the described polymer-coated hard-shell capsules are for instance: analgesics, antibiotics or anti-infectives, antibodies, antiepileptics, antigens from plants, antirheumatics, benzimidazole derivatives, beta-blocker, cardiovascular drugs, chemotherapeutics, CNS drugs, digitalis glycosides, gastrointestinal drugs, e.g. proton pump inhibitors, enzymes, hormones, liquid or solid natural extracts, oligonucleotides, peptide hormones proteins, therapeutic bacteria, monoclonal microbials, microbial components, peptides, proteins and their (metal) salts i.e. aspartates, chlorides, orthates, urology drugs, vaccines.

Further examples of drugs that may be used as fill-in for the described polymer-coated hard-shell capsules are for instance acamprosat, aescin, amylase, acetylsalicylic acid, adrenalin, 5-amino salicylic acid, aureomycin, bacitracin, balsalazine, beta carotene, bicalutamid, bisacodyl, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormone (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, olsalazine, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, trypsine, valproic acid, vasopressin, vitamins, zinc, including their salts, derivatives, polymorphs, isomorphs, or any kinds of mixtures or combinations thereof.

It is evident to a skilled person that there is a broad overlap between the terms pharmaceutically and nutraceutically active ingredients, excipients and compositions respectively a pharmaceutical or a nutraceutical dosage form. Many substances listed as nutraceuticals may also be used as pharmaceutical active ingredients. Depending on the specific application and local authority legislation and classification, the same substance may be listed as a pharmaceutically or a nutraceutically active ingredient respectively a pharmaceutical or a nutraceutical composition or even both.

Nutraceuticals are well known to the skilled person. Nutraceuticals are often defined as extracts of foods claimed to have medical effects on human health. Thus, nutraceutical active ingredients may display pharmaceutical activities as well: Examples for nutraceutically active ingredients may be resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Thus, it is clear that many substances listed as nutraceuticals may also be used as pharmaceutically active ingredients.

Typical nutraceuticals or nutraceutically active ingredients that may be used as fill-in for the described polymer-coated hard-shell capsules may also include probiotics and prebiotics. Probiotics are living microorganisms believed to support human or animal health when consumed. Prebiotics are nutraceuticals or nutraceutically active ingredients that induce or promote the growth or activity of beneficial microorganisms in the human or animal intestine.

Examples for nutraceuticals are resveratrol from grape products, omega-3-fatty acids or (pro)anthocyanines, for instance from blueberries or black currents, as antioxidants, soluble dietary fiber products, such as psyllium seed husk for reducing hypercholesterolemia, broccoli (sulphane) as a cancer preservative, and soy or clover (isoflavonoids) to improve arterial health. Other examples for nutraceuticals are flavonoids, antioxidants, alpha-linoleic acid from flax seed, beta-carotene from marigold petals or anthocyanins from berries. Sometimes the expressions neutraceuticals or nutriceuticals are used as synonyms for nutraceuticals.

Preferred biologically active ingredients are metoprolol, mesalamine and omeprazole.

Polymer Coated Hard-Shell Capsule

The invention is concerned with a process for preparing a polymer-coated hard-shell capsule, comprising a body and a cap. In the closed stage the cap overlaps the body either in a pre-locked state or in a final-locked state. The hard-shell capsule is usually commercially available in the pre-locked state and then preferably spray-coated with a coating solution or dispersion comprising one or more anionic cellulose(s), ethyl cellulose and/or one or more starches comprising at least 35% by weight amylose to create a coating layer which covers the outer surface of the hard-shell capsule in the pre-locked state.

Hard-Shell Capsules

Hard-shell capsules for pharmaceutical or nutraceutical purposes are well known to a skilled person. A hard-shell capsule is a two-piece encapsulation capsule comprising of the two capsule halves, called the body and the cap. The capsule body and cap material is usually made from a hard and sometimes brittle material. The hard-shell capsule comprises a body and a cap. Body and cap are usually of a one end open cylindrical form with closed rounded hemispherical ends on the opposite end. The shape and size of the cap and body are such that the body can be pushed telescopically with its open end into the open end of the cap.

The body and the cap comprise a potential overlapping matching area (overlap area) outside the body and inside the cap which partially overlap when the capsule is closed in the pre-locked state and totally overlap in the final-locked state. When the cap is partially slid over the overlapping matching area of the body the capsule is in the pre-locked state. When the cap is totally slid over the overlapping matching area of the body the capsule is in the final-locked state. The maintenance of the pre-locked state or of the final-locked state is usually supported by snap-in locking mechanisms of the body and the cap such as matching encircling notches or dimples, preferably elongated dimples.

Usually the body is longer than the cap. The outside overlapping area of the body can be covered by the cap in order to close or to lock the capsule. In the closed state the cap covers the outside overlap area of the body either in a pre-locked state or in a final-locked state. In the final-locked state the cap covers the outside overlap area of the body in total, in the pre-locked state the cap overlaps the outside overlapping area of the body only partially. The cap can be slid over the body to be fixed in usually one of two different positions in which the capsule is closed either in a pre-locked state or in a final-locked state.

Hard-shell capsules are commercially available in different sizes. Hard-shell capsules are usually delivered as empty containers with the body and cap already positioned in the pre-locked state and on demand as separate capsule halves, bodies and caps. The pre-locked hard-shell capsules can be provided to a capsule-filling machine, which performs the opening, filling and closing of the capsules into the final-locked state. Usually hard-shell capsules are filled with dry materials, for instance with powders or granules comprising a biologically active ingredient.

The cap and body are provided with closure means that are advantageous for the pre-locking (temporary) and/or final locking of the capsule.

Therefore, elevated points may be provided on the inner wall of the cap and somewhat larger indented points are provided on the outer wall of the body, which are arranged so that when the capsule is closed the elevations fit into the indentations. Alternatively, the elevations may be formed on the outer wall of the body and the indentations on the inner wall of the cap. Arrangements in which the elevations or indentations are arranged in a ring or spiral around the wall are also possible. Instead of the point-like configuration of the elevations and indentations, these may encircle the wall of the cap or body in an annular configuration, although advantageously recesses and openings are provided which enable an exchange of gases into and out of the capsule interior.

One or more elevations may be provided in an annular arrangement around the inner wall of the cap and the outer wall of the body such that, in the final-locked position of the capsule, an elevation on the cap is located adjacent to an elevation on the body. Sometimes elevations are formed on the outside of the body close to the open end and indentations are formed in the cap close to the open end such that the elevations on the body latch into the indentations in the cap in the final-locked position of the capsule. The elevations may be such that the cap can be opened in the pre-locked state at any time without damage to the capsule or, alternatively, so that once it has been closed the capsule cannot be opened again without destroying it.

Capsules with one or more such latching mechanisms (latches, for instance two circulating grooves) are preferred.

More preferred are capsules with at least two such latching means which secure the two capsule parts to different degrees. In a part of this kind, a first latching (dimples or circulating notches) means may be formed close to the openings in the capsule cap and the capsule body and a second latching (circulating notches) can be shifted somewhat further towards the closed end of the capsule parts. The first latching means secure the two capsule parts less strongly than the second does. This variant has the advantage that after the production of the empty capsules the capsule cap and capsule body can initially be pre-locked joined together using the first latching mechanism. In order to fill the capsule, the two capsule parts are then separated again. After filling, the two capsule parts are pushed together until the second set of latches firmly secures the capsule parts in a final-locked state.

Preferably, the body and the cap of the hard-shell capsule are comprising each encircling notches and/or dimples in the area, where the cap can be slid over the body. Encircling notches of the body and dimples of the cap match to each other to provide a snap-in or snap into-place mechanism. The dimples may be circular or elongated (oval) in the longitudinal direction.

Encircling notches of the body and encircling notches of the cap (closely matched rings) also match to each other to provide a snap-in or snap into-place mechanism. This allows the capsule to be closed by a snap-into-place mechanism either in a pre-locked state or in a final-locked state. Preferably, matching encircling notches of the body and elongated dimples of the cap are used to fix the body and the cap to each other in the pre-locked state. Matching encircling notches of the body and the cap are preferably used to fix or lock the body and the cap to each other in the final-locked state.

The area where the cap can be slid over the body may be called the overlapping area of the body and the cap or briefly the overlap area. If the cap overlaps the body only partially, maybe to 20 to 90 or 60 to 85% of the overlap area, the hard-shell capsule is only partially closed (pre-locked). Preferably, in the presence of a locking mechanism, like matching encircling notches and/or dimples in body and cap, the partially closed capsule may be called pre-locked. When the capsule is polymer-coated in the pre-locked state the coating will cover the completely outer surface including that part of the overlap area of the body and cap that is not overlapped by the cap in this pre-locked state. When the capsule is polymer-coated in the pre-locked state and then closed to the final-locked state the coating of that part of the overlap area of the body and cap that was not overlapped by the cap in the pre-locked state will then become covered by the cap. The presence of that part of the coating which is then enclosed in the final-locked state between the body and the cap is sufficient for the hard-shell capsule to be tightly sealed. This was by no means to be foreseen.

If the cap overlaps the total overlapping area of the body, the hard-shell capsule is finally closed or in the final-locked state. Preferably, in the presence of a locking mechanism, like matching encircling notches and/or dimples in body and cap, the finally closed capsule may be called final-locked.

Usually dimples are preferred for the fixing the body and the cap in the pre-locked state. As a non-binding rule the matching area of dimples is smaller than the matching area of encircling notches. Thus snapped-in dimples may be snapped-out again by applying less forces than those that would be necessary to snap-out a snapped-in fixation by matching encircling notches.

The dimples of the body and cap are located in the area where the cap can be slid over the body matching to each other in the pre-locked state by a snap in or snap into-place mechanism. There may be for example 2, 4, or preferably 6 notches or dimples located distributed circular around the cap.

Usually the dimples of the cap and the encircling notches of the body are in the area where the cap can be slid over the body, matching to each other so that they allow the capsule to be closed by a snap-into-place mechanism in the pre-locked state. In the pre-locked state, the hard-shell capsule can be re-opened manually or by a machine without damaging, because the forces needed to open are comparatively low. So, the "pre-locked state" is sometimes designated also as "loosely capped".

Usually the encircling notches or matching locking rings of the body and the cap are in the area where the cap can be slid over the body, matching to each other so that they allow the capsule to be closed by a snap-into-place mechanism in the final-locked state. In the final-locked state, the hard-shell capsule cannot or can be only hardly be re-opened manually or by a machine without damaging, because the forces needed to open are comparatively high.

Usually the dimples and the encircling notches are formed in the capsule body or capsule cap. When the capsule parts provided with these elevations and indentations are fitted into one another, ideally defined uniform gaps of from 10 microns to 150 microns, more particularly 20 microns to 100 microns, are formed along the contact surface between the capsule body and the capsule cap placed thereon.

Preferably, the body of the hard-shell capsule comprises a tapered rim. The tapered rim prevents the rims of the body and the cap to collide and becoming damaged when the capsule is closed manually or by a machine.

In contrast to a hard-shell capsule, a soft-shell capsule is a welded one-piece encapsulation capsule. A soft gel capsule is often made from blow molded soft gelling substances and is usually filled with liquids comprising a biologically active ingredient by injection. The invention is not concerned with welded soft-shell one-piece encapsulation capsules.

Sizes of Hard Shell Capsules

The polymer coated hard-shell capsule may be derived from an uncoated hard-shell capsule of the standard size 000, 00, 0, 1, 2, 3, 4, 5 or 9.

A closed, final-locked hard-shell capsule may have a total length in the range from about 5 to 40 mm. The diameter of the cap may be in the range from about 4 to 12 mm. The diameter of the body may be in the range from about 2 to 11 mm. The length of the cap may be in the range from about 4 to 20 mm and that of the body in the range from 8 to 30 mm. The fill volume may be between about from 0.1 to 2 ml. The difference between the pre-locked length and the final-locked length may be about 1 to 5 mm.

Capsules can be divided into standardized sizes for example from sizes 000 to 5. A closed capsule of size 000 has, for example, a total length of about 28 mm with an outer diameter of the cap of about 9.9 mm and an outer diameter of the body of about 9.5 mm. The length of the cap is about 14 mm, that of the body about 22 mm. The fill volume is about 1.4 ml.

A closed capsule of size 5 has, for example, a total length of about 10 mm and an outer diameter of the cap of about 4.8 mm and an outer diameter of the body of about 4.6 mm. The length of the cap is about 5.6 mm, that of the body about 9.4 mm. The fill volume is about 0.13 ml.

A size 0 capsule may show a length of about 23 to 24 mm in the pre-locked stage and of about 20.5 to 21.5 mm in the final-locked stage. Thus, the difference between the pre-locked length and the final-locked length may be about 2 to 3 mm.

Material of the Body and the Cap

The material of the body and the cap comprises an ethyl-, methyl- or propyl-ether of cellulose starch or pullulan. Cellulose-ethers are derivates of cellulose in which the hydrogen atoms of the hydroxyl groups are partially or fully substituted by alkyl groups, such as ethyl-, methyl- or propyl-groups. These derivates of cellulose are well known to skilled person in pharmacy and galenic. Suitable materials are methyl cellulose (MC), ethyl cellulose (EC), hydroxyethyl cellulose (HEC), hydroxypropyl cellulose (HPC) and/or hydroxypropyl methyl cellulose (HPMC). Preferred is hydroxypropyl methyl cellulose (HPMC).

Coating Layer

The hard-shell capsule is provided in the pre-locked state and spray-coated with a coating solution, suspension or dispersion to create the corresponding coating layer which covers the outer surface of the hard-shell capsule in the pre-locked state.

The coating layer may be a single layer or may comprise or consist of two or more individual layers.

The hard-shell capsule is coated with a coating layer that covers the hard-shell capsule in the pre-locked state. The coating layer is comprising one or more anionic cellulose(s), ethyl cellulose and/or one or more starches comprising at least 35% by weight amylose, preferably with a glass transition temperature $T_{gm}$ of 130° C. or less (determined by Differential Scanning Calorimetry (DSC) according to ISO 11357-2:2013-05), wherein the coating layer is present in an amount of about 1 to 5.8, preferably 2 to 5 mg/cm$^2$, wherein a dried film corresponding to the composition of the coating layer shows an elongation at break of about 15 to 500%. The elongation at break is determined with a test sample (sample type 1B, 20 mm/min) according to DIN EN ISO 527-3:2018, February 2019.

The coating layer, which may be a single layer or may comprise or consist of two or more individual layers, may comprise in total 10 to 100, 20 to 95, 30 to 90% by weight of comprising one or more anionic cellulose(s), ethyl cellulose and/or one or more starches comprising at least 35% by weight amylose.

The coating layer, which may be a single layer or may comprise or consist of two or more individual layers, may comprise in total 90 to 0, 80 to 5, 70 to 10% by weight of pharmaceutically or nutraceutical excipients.

The comprising one or more anionic cellulose(s), ethyl cellulose and/or one or more starches comprising at least 35% by weight amylose and the pharmaceutical or nutraceutical excipients may add up to 100%.

Anionic Cellulose(s)

The anionic celluloses may be selected from carboxymethyl ethyl cellulose and its salts, cellulose acetate phthalate (CAP), cellulose acetate succinate (CAS), cellulose acetate trimellitate (CAT), hydroxypropyl methyl cellulose phthalate (HPMCP, HP-50, HP-55) and hydroxypropyl methyl cellulose acetate succinate (HPMCAS-LF, -MF, -HF) or any mixtures thereof.

The glass transition temperature $T_{gm}$ of hydroxypropyl methyl cellulose phthalate is about 132 to 138° C. (type HP-55 about 133° C., type HP-50 about 137° C.).

The glass transition temperature $T_{gm}$ of hydroxypropyl methyl cellulose acetate succinate (HPMCAS) is about 120° C. (AquaSolve™ L HPMCAS 119° C., AquaSolve™ M HPMCAS 120° C., AquaSolve™ H HPMCAS 122° C.).

Ethyl Cellulose

Ethyl cellulose is a derivative of cellulose in which some of the hydroxyl groups of the repeating glucose units are converted into ethyl ether groups. Ethyl cellulose may be used as a delayed release coating material for the capsules as disclosed. The glass transition temperature $T_{gm}$ of ethyl cellulose may be in the range of about 128 to 130° C. (Hui Ling Lai et al. Int. J. Pharmaceuticals 386 (2010) 178-184)

Starches Comprising at Least 35% by Weight Amylose

Starches comprising at least 35% by weight amylose are commercially available as starch from corn or maize origin.

Starches comprising at least 35% by weight amylose are known for example from EP 1296658B1. This type of chemically modified (acetylated) starch with a high content in amylose is obtained through a pre-gelation process. These starches show a high mechanical resistance for the production of capsules and coatings for solid formulations used in various application in the fields of pharmaceuticals or nutraceuticals.

The glass transition temperature $T_{gm}$ of starches comprising at least 35% by weight amylose may be in the range of about 52 to 60° C. (Peng Liu et al., J. Cereal Science (2010) 388-391).

Glass Transition Temperature $T_{gm}$

The one or more anionic cellulose(s), ethyl cellulose and/or one or more starches comprising at least 35% by weight amylose may show glass transition temperatures up to about 150° C., which is comparatively high. The required elasticity (elongation at break) of the coating layer may be realized by addition of comparatively high amounts or combinations of plasticizers and/or emulsifiers and/or detacking agents.

In a preferred embodiment the inventors have found that a coating layer may comprise one or more anionic cellulose(s), ethyl cellulose and/or one or more starches comprising at least 35% by weight amylose) with a glass transition temperature $T_{gm}$ of 130 or less, preferably 127° C. or less, more preferably from 50 to 130 or from 50 to 127° C. These polymers are less brittle and more flexible which supports the coating layer to resist against the high mechanical forces occurring during the processing in a capsule filling machine. In combination with these polymers, the required elasticity (elongation at break) of the coating layer may be realized by addition of less amounts of plasticizers and/or emulsifiers and/or detacking agents. In this embodiment hydroxypropyl methyl cellulose phthalate may be generally excluded.

Thus, the coating layer may comprise one or more anionic cellulose(s), ethyl cellulose and/or one or more starches comprising at least 35% by weight amylose with a glass transition temperature $T_{gm}$ of 130 or less, preferably 127° C. or less, more preferably from 50 to 127° C.

Thus, the coating layer may comprise one or more anionic cellulose(s), ethyl cellulose and/or one or more starches comprising at least 35% by weight amylose with a glass transition temperature $T_{gm}$ of 127° C. or less, preferably from 50 to 127° C., wherein hydroxypropyl methyl cellulose phthalate is excluded.

The glass transition temperature $T_{gm}$ is determined by Differential Scanning Calorimetry (DSC) according to ISO 11357-2:2013-05. The determination is performed with a heating rate of 20 k/min. The glass transition temperature $T_{gm}$ was determined by half step height method as described in section 10.1.2 of DIN EN ISO 11357-2.

Thickness of the Coating Layer

The coating layer is present in an amount of about 1 to 5.8, preferably 2 to 5 mg/cm$^2$. The thickness of the coating layer may be determined by calculation of the amount of the coating material applied to the empty pre-locked capsules, for instance in a spray coating process, in relation to the surface area of the empty pre-locked capsules (see also examples 1 and 2, The FIGURE). The coating layer may be a single layer or may comprise or consist of two or more individual layers. In the case of two or more individual layers, the thickness of the individual layers cumulating to the thickness of the coating layer in total.

Elongation at Break

The inventors have found that processing in a capsule filling machine requires a certain elasticity of the coating layer. The elasticity of the coating layer may be characterized in that a dried film corresponding to the composition of the coating layer shows an elongation at break of about 15 to 500, preferably 20 to 250%.

Elongation at break may be determined according to DIN EN ISO 527-1: 2012-06 (General principles, especially chapter 8) and 527-3:2018, February 2019, determination of tensile properties for films and sheets with a thickness below 1,000 µm. The elongation at break is the percentage increase in length that a material will achieve before breaking. This figure is shown as the percentage. Suspension of the compositions for the coating layer are spread on a glass plate and dried to a film of 250 µm thickness. The elongation at break is determined with a test sample (sample type 1B, 20 mm/min) according to DIN EN ISO 527-3:2018, February 2019.

Example for the Preparation and Testing of Polymer Films:

Formulation

Polymer dispersion or suspension with 9 g solids, used for a 250 µm film after drying.

Equipment

Glass plate 20 cm×20 cm with a surrounding of 1 cm glass strips of 0.5-0.7 cm height, resulting in a free preparation area of 361 cm$^2$. This glass plate is in addition covered with a self-adhesive Polytetrafluoroethylen foil (i.e. Tygaflor®).

Processing

The polymer and diluent are mixed on a magnetic stirrer for 10 minutes at low speed. The polymer solution or suspension needs to be air free to avoid voids in the polymer foil. The Polytetrafluoroethylen covered glass plate is levelled in an oven and the polymer solution or dispersion is poured into it. The mixture is dried for approximately 4 days at 40° C. After drying the foils or sheets will be conditioned for 16 hours at 23° C. and 50% relative humidity.

The resulting film thickness is approx. 250 µm.

The same method can be used to manufacture films of coating suspensions. In this case the coating suspension is prepared like usually (e.g. using an ultra turrax). An aliquot amount for 9 g of total solids (including formulation excipients) is diluted with demineralized water up to a total amount of 100 g.

Pharmaceutical or Nutraceutical Excipients

Pharmaceutical or nutraceutical excipients are well known to a skilled person and often formulated along with the biologically active ingredient contained in the coated hard-shell capsule and/or with the polymer coating of the hard-shell capsule as disclosed herein. All pharmaceutical or nutraceutical excipients used must be toxicologically safe to be used in pharmaceuticals or nutraceuticals without risk for patients or consumers.

Pharmaceutically or nutraceutically acceptable excipients, may be selected from the group of antioxidants, brighteners, binding agents, flavouring agents, flow aids, fragrances, glidants, penetration-promoting agents, pigments, plasticizers, polysaccharide polymers, emulsifiers, pore-forming agents or stabilizers or combinations thereof.

A pharmaceutically or nutraceutically acceptable excipient is an excipient, which is allowed to be used for the application in the pharmaceutical or nutraceutical field.

The pharmaceutical or nutraceutical excipients may preferably comprise one or more plasticizers and/or one or more detacking agents.

The addition of plasticizer(s) to one or more anionic cellulose(s), ethyl cellulose and/or one or more starches comprising at least 35% by weight amylose is usually lowering the glass transition temperature of the mixture, elongation at break is usually increased. The effect may depend on the type and amount of plasticizer that is added. Plasticizer(s) may be selected from the groups of alkyl citrates, glycerol esters, alkyl phthalates, alkyl sebacates, sucrose esters, sorbitan esters, glycerol, propylene glycol and polyethylene glycols. Preferred plasticizers are triethyl citrate, polyethylene glycol 20,000 and propylene glycol. The amount of plasticizer added may be in the range of 2 to 50, preferably 5 to 30% by weight calculated on the weight of the one or more anionic cellulose(s), ethyl cellulose and/or one or more starches comprising at least 35% by weight amylose.

The addition of detacking agents to the comprising one or more anionic cellulose(s), ethyl cellulose and/or one or more starches comprising at least 35% by weight amylose is usually decreasing the tackiness of the mixture respectively of the coated film. Detacking agent(s) may be selected from Ca-stearate or Mg-stearate, glycerol monostearate and talc. The amount of detacking agent added may be in the range of 2 to 60, preferably 5 to 55% by weight calculated on the weight of the one or more anionic cellulose(s), ethyl cellulose and/or one or more starches comprising at least 35% by weight amylose.

The coating layer may further comprise an emulsifier, preferably polysorbate 80. The amount of emulsifier added may be in the range of 1 to 30, preferably 3 to 25% by weight calculated on the weight of the one or more anionic cellulose(s), ethyl cellulose and/or one or more starches comprising at least 35% by weight amylose.

Top Coat

The coating layer may comprise or include an additional top coat in an amount of 0.2 to 0.8 mg/cm$^2$, comprising hydroxypropyl methyl cellulose and optionally pigments or colorants. The top coat may also comprise further excipient polymers such as polyvinyl alcohol (PVA), hydroxy propyl cellulose (HPC) or Opadry®. Preferably the top coat does not comprise essential amounts or no one or more anionic cellulose(s), ethyl cellulose and/or one or more starches comprising at least 35% by weight amylose at all.

Capsule Filling Machine

The polymer-coated hard-shell capsule is provided in the pre-locked state to a capsule-filling machine, which performs the steps of separating the body and the cap, filling the body with the fill and rejoining the body and the cap in the final-locked state.

The capsule filling machine used may be a capsule filling machine, preferably a fully automated capsule filling machine, that is capable to produce filled and closed capsules at a speed with an output of 1,000 or more filled and finally closed capsules per hour. Capsule filling machines, preferably fully automated capsule filling machines, are well known in the art and commercially available from several companies. A suitable capsule filling machine as used in the examples may be for instance ACG, model AFT Lab.

The capsule filling machine used may be preferably operated at a speed with an output of 1,000 or more, preferably 10,000 or more, 100,000 or more, 10,000 up to 500,000, filled and finally closed capsules per hour.

Capsule Filling Machine General Operations

Before the capsule filling process, the capsule filling machine is provided with a sufficient number or amount of pre-coated hard-shell capsules in the pre-locked state. The capsule filling machine is also provided with sufficient amounts of fill to be filled in during operation.

The hard-shell capsules in the pre-locked state may fall by gravity into feeding tubes or chutes. The capsules may be uniformly aligned by mechanically gauging the diameter differences between the cap and the body. The hard-shell capsules are then usually fed, in proper orientation, into a two-section housing or brushing.

The diameter of the upper bushing or housing is usually larger than the diameter of the capsule body bushing; thus, the capsule cap may be retained within an upper bushing while the body is pulled into a lower bushing by vacuum. Once the capsule is opened/the body and the cap are separated, the upper and lower housing or bushing are separated to position the capsule body for filling.

The open capsule body is then filled with the fill. Various types of filling mechanisms may be applied, with respect to the different fillings such as granules, powders, pellets or mini-tablets. Capsule filling machines in general employ a variety of mechanisms to handle the various dosage ingredients as well as various numbers of filling stations. The dosing systems are usually based on volumetric or amounts of fills governed by the capsule size and capacity of the capsule body. The empty capsule manufacturers usually provide reference tables that indicate the volume capacity of their capsule body and the maximum fill weight for different capsule sizes based on the density of the fill material. After the filling, the body and the cap are rejoined by the machine in the final-locked state or position.

Example 1—Determination of Capsule Overlap

Dimensions and tolerances of different commercially available capsules with respect to mean difference between pre-locked and locked lengths.

TABLE 1

| | Hard Shell Capsule Dimensions (1/2) | | | | | | | | |
|---|---|---|---|---|---|---|---|---|---|
| | Manufacturer | | | | | | | | |
| | Capsugel | | | Capsugel | | | Capsugel | | |
| | Color | | | | | | | | |
| | Transparent | | | White | | | Transparent | | |
| | Size | | | | | | | | |
| | #0 Vcaps ® plus | | | #0 Vcaps ® plus | | | #1 Vcaps ® plus | | |
| | Locking stage | | | | | | | | |
| | Un-locked | pre-locked | Final-Locked | Un-locked | pre-locked | Final Locked | Un-locked | pre-locked | Final Locked |
| Length [mm] | 29.16 | 23.65 | 21.38 | 29.16 | 23.76 | 20.91 | 26.39 | 21.19 | 19.03 |
| SD [mm] | | 0.19 | 0.2 | | 0.16 | 0.17 | | 0.15 | 0.07 |
| Minimum [mm] | | 23.25 | 21 | | 23.43 | 20.67 | | 20.95 | 18.9 |
| Maximum [mm] | | 23.95 | 21.7 | | 23.99 | 21.31 | | 21.4 | 19.15 |
| Overlap length [mm] | | 5.51 | 2.27 | | 5.4 | 2.85 | | 5.2 | 2.16 |
| Total Overlap length [mm] | | 7.78 | | | 8.25 | | | 7.36 | |
| Overlap level | | 71% | 100% | | 65% | 100% | | 71% | 100% |

TABLE 2

| | Hard Shell Capsule Dimensions (2/2) | | | | | | | | |
|---|---|---|---|---|---|---|---|---|---|
| | Manufacturer | | | | | | | | |
| | Capsugel | | | ACG | | | ACG | | |
| | Color | | | | | | | | |
| | Transparent | | | Transparent | | | White | | |
| | Size | | | | | | | | |
| | #3 Vcaps ® plus | | | #0 Naturecaps | | | #0EL Naturecaps | | |
| | Locking stage | | | | | | | | |
| | Un-locked | pre-locked | Final Locked | Un-locked | pre-locked | Final Locked | Un-locked | pre-locked | Final Locked |
| Length [mm] | 21.67 | 17.69 | 15.74 | 29.2 | 23.04 | 20.92 | 32 | 25.17 | 22.87 |
| SD [mm] | | 0.16 | 0.17 | | 0.12 | 0.16 | | 0.07 | 0.17 |

TABLE 2-continued

| | Hard Shell Capsule Dimensions (2/2) | | | | | | | | |
|---|---|---|---|---|---|---|---|---|---|
| | Manufacturer | | | | | | | | |
| | Capsugel | | | ACG | | | ACG | | |
| | Color | | | | | | | | |
| | Transparent | | | Transparent | | | White | | |
| | Size | | | | | | | | |
| | #3 Vcaps ® plus | | | #0 Naturecaps | | | #0EL Naturecaps | | |
| | Locking stage | | | | | | | | |
| | Un-locked | pre-locked | Final Locked | Un-locked | pre-locked | Final Locked | Un-locked | pre-locked | Final Locked |
| Minimum [mm] | | 17.39 | 15.23 | | 22.65 | 20.68 | | 25.01 | 22.59 |
| Maximum [mm] | | 17.94 | 15.98 | | 23.21 | 21.22 | | 25.29 | 23.1 |
| Overlap length [mm] | | 3.98 | 1.95 | | 6.16 | 2.12 | | 6.83 | 2.3 |
| Total Overlap [mm] | | 5.93 | | | 8.28 | | | 9.13 | |
| Overlap level | | 67% | 100% | | 74% | 100% | | 75% | 100% |

Example 2—Surface Area Calculation and Colon Targeting Coating of Pre-Locked Capsules in Drum Coater Since a certain coating layer thickness is required to achieve the desired film functionality, the required amount of coating material depends on the surface area of the substrate. For this reason, coating quantities are expressed as mg of total dry substance per cm² of substrate surface area. Below the equation of pre-locked capsule surface are is described considering the mean difference between the pre-locked state and the accumulated length of the separate capsule halves, body and cap.

$$A_{\frac{1}{2}Sphere} = 2\left(\frac{d}{2}\right)^2 \pi$$

$$A_{Cylinder,body} = 2\pi\left(\frac{d}{2}\right)(h - h_{overlap})$$

$$A_{Cylinder,cap} = 2\pi\left(\frac{d}{2}\right)h$$

$$A_{Capsule-segment} = A_{\frac{1}{2}Sphere} + A_{Cylinder}$$

$$A_{Pre-locked\ capsule} = A_{Body} + A_{Cylinder}$$

$A$ = Surface Area $h$ = Length $d$ = Diameter

Calculation Example 2 for the Calculation of the Outer Capsule Surface in the Pre-Locked State

TABLE 3

| Vcaps ® Plus Capsule Specifications: | | | | | | | | | |
|---|---|---|---|---|---|---|---|---|---|
| Size | 00el | 00 | 0el | 0 | 1 | 1el | 2 | 3 | 4 |
| Weight | | | | | | | | | |
| Weight [mg] | 130 | 122 | 107 | 96 | 76 | 81 | 61 | 47 | 38 |
| Tolerance [mg] | ±10 | ±7 | ±7 | ±6 | ±5 | ±5 | ±4 | ±3 | ±3 |
| Length of the capsules halves (body and cap) | | | | | | | | | |
| Body [mm] | 22.20 | 20.22 | 20.19 | 18.44 | 16.61 | 17.70 | 15.27 | 13.59 | 12.19 |
| Tolerance [mm] | ±0.46 | ±0.46 | ±0.46 | ±0.46 | ±0.46 | ±0.46 | ±0.46 | ±0.46 | ±0.46 |
| Cap [mm] | 12.95 | 11.74 | 11.68 | 10.72 | 9.78 | 10.49 | 8.94 | 8.08 | 7.21 |
| Tolerance [mm] | ±0.46 | ±0.46 | ±0.46 | ±0.46 | ±0.46 | ±0.46 | ±0.46 | ±0.46 | ±0.46 |
| External diameter | | | | | | | | | |
| Body [mm] | 8.18 | 8.18 | 7.34 | 7.34 | 6.63 | 6.63 | 6.07 | 5.57 | 5.05 |
| Cap [mm] | 8.53 | 8.53 | 7.65 | 7.64 | 6.91 | 6.91 | 6.35 | 5.82 | 5.32 |
| Overall length in the final-locked state | | | | | | | | | |
| Length [mm] | 25.3 | 23.30 | 23.5 | 21.70 | 19.40 | 20.40 | 18.00 | 15.90 | 14.30 |
| Tolerance [mm] | ±0.30 | ±0.30 | ±0.30 | ±0.30 | ±0.30 | ±0.30 | ±0.30 | ±0.30 | ±0.30 |

The FIGURE shows a schematic drawing of the body (left) and the cap (right) of a Vcaps® Plus size 1 hard-shell capsule with the relevant dimensions in mm. The dimensions are used in the calculation example 9 for the calculation of the outer capsule surface in the pre-locked state. The dimensions are:

Body: length=16.61 mm, cylinder (length of the cylindrical part)=13.29 mm, outer diameter=6.63 mm Cap: length=9.78 mm, cylinder (length of the cylindrical part)=6.32 mm, outer diameter=6.91 mm $$A_{\frac{1}{2} Sphere, Body} = 2\left(\frac{6.63}{2}\right)^2 \pi = 69.05 \text{ [mm}^2\text{]}$$

$$A_{Cylinder, Body} = 2\pi\left(\frac{6.63}{2}\right)(13.29 - 5.2) = 16855 \text{ [mm}^2\text{]}$$

$$A_{\frac{1}{2} Sphere, Cap} = 2\left(\frac{6.91}{2}\right)^2 \pi = 75.00 \text{ [mm}^2\text{]}$$

$$A_{Cylinder, Cap} = 2\pi\left(\frac{6.91}{2}\right)6.32 = 137.20 \text{ [mm}^2\text{]}$$

$$A_{Capsule-body} = 69.05 + 168.50 = 237.55 \text{ [mm}^2\text{]}$$

$$A_{Capsule-cap} = 75.00 + 137.20 = 212.20 \text{ [mm}^2\text{]}$$

$$A_{Pre-locked\ capsule} = 237.55 + 212.20 = 449.75 \text{ [mm}^2\text{]}$$

TABLE 4

Capsule Surface Area

| Parameter | Body | Cap |
|---|---|---|
| $A_{1/2\ Sphere}$ [mm$^2$] | 69.05 | 75.00 |
| $A_{Cylinder}$ [mm$^2$] | 168.50 | 137.20 |
| $A_{Segment}$ [mm$^2$] | 237.55 | 212.20 |
| $A_{Pre-locked\ capsule}$ [mm$^2$] | 449.75 | |

Example 3 (Inventive)—Coating of Pre-Locked Empty Capsules with Anionic Cellulose Polymer in a Drum Coater, Followed by Capsule Filling Using an Automatic Capsule Filling Machine HPMCAS (AQOAT® AS LF) polymer was dissolved under stirring for about 30 minutes in a solvent mixture of Ethanol and water. Triethyl citrate was added to the mixture and stirred for another 15 minutes. This solution was used to coat the empty Kcaps® HPMC hard capsules (size #0) in a pre-locked state, using a drum coater (Neocota 5D).

TABLE 5

Formulation Example 3—Coating on Kcaps ® HPMC Size 0 capsules (Batch size 90 g i.e. 833 capsules)

| Material | Composition | Solid Composition Percentage |
|---|---|---|
| HPMCAS (AQOAT ® AS LF) | 2.0 mg/cm$^2$ | 76.9% |
| Triethyl citrate | 30% on ds* | 23.1% |
| Ethanol: Water (80:20) | q.s. to 5% w/w solids | |
| Solid content | 5% w/w | |
| Total solid weight gain | 2.60 mg/cm$^2$ | |

*Quantity based on dry polymer substance [%]

TABLE 6

Process Parameters for Example 3

| Parameter | Value |
|---|---|
| Machine | Neocota 5D |
| Batch size [g] | 90 |
| Nozzle bore [mm] | 0.8 |
| Internal tube diameter [mm] | 3.0 |
| Peristaltic pump | Flowtrietec |
| Atomizing pressure [bar] | 1.5 |
| Flat pattern pressure [bar] | 0.5 |
| Room temperature [° C.] | 20-25 |
| Room humidity [% r.h.] | 50-60 |
| Pan speed [rpm] | 11 |
| Product temperature [° C.] | 30-38 |
| Spray rate [g/min/kg] | 11-22 |

Encapsulation Parameters/Observations 568 mg of immediate release metoprolol pellets (40% active) were filled into the polymer coated pre-locked capsules using automatic capsule filling machine AFTLAB (ACG) with a pellets filling set up using standard format size 0 tooling for capsule opening, transport, filling and closing. The machine output was set to 5,000-5,400 cps/hour.

Capsules filled in the automatic capsule filling machine, were coated with 2.0 mg/cm$^2$ polymer weight gain corresponding with 2.6 mg/cm$^2$ total solid weight gain.

Process Observations

Capsule filling operation was smooth, capsules body and caps were easily opened and fit well into the machine parts. Yield of 96.8% could be achieved (3.2% capsules were rejected by the machine) on automatic capsule filling machine.

Dissolution Test

Method:

Apparatus: Labindia DS 8000 Paddle Apparatus (USP II) with sinkers

Detection method: HPLC analysis

Temperature: 37.5° C.

Media I: 500 ml 0.1 N HCL for 2 hours

Media II: 500 ml KH2PO4 pH 6.8 buffer for 1 hour

Paddle speed: 50 rpm

TABLE 7

Dissolution Results (n = 6) Example 3

| Media | Time [min] | Mean [% released] | Standard Deviation |
|---|---|---|---|
| 0.1N HCL | 0 | 0.0 | 0.0 |
| 0.1N HCL | 120 | 0.1 | 0.2 |
| pH6.8 | 135 | 85.2 | 5.2 |
| pH6.8 | 150 | 93.5 | 0.5 |
| pH6.8 | 165 | 93.9 | 0.4 |
| pH6.8 | 180 | 93.9 | 0.5 |

Film Preparation and Testing:

HPMCAS (AQOAT® AS LF) polymer and triethyl citrate (30% based on dry polymer substance) were dissolved under stirring for about 24 hours in a solvent mixture of Ethanol and water (80:20) (9.0 g solid content, solid composition percentage ration HPMCAS to triethyl citrate [76.9% to 23.1%]). The polymer solution was poured onto a Polytetrafluoroethylen covered glass plate and dried for 4 days at 40° C. After drying the film was conditioned for 16 hours at 23° C. and 50% relative humidity. The resulting film thickness was approx. 250 μm. Elongation at break was determined according to DIN EN ISO 527-3:2019-02. An elongation at break value of 22.5% was obtained.

Conclusion

The film flexibility of the coating layer composition was sufficient to allow smooth capsule filling using the automatic capsule filling machine without damage of the capsule coating layer meeting the requirements of the US pharmacopeia (USP42-NF37) according to monograph <711> Dissolution of delayed release dosage forms acceptance table 3 and 4.

Example 4 (Comparative)—Coating of Pre-Locked Empty Capsules with a Combination of Anionic Cellulose Polymer & Ethyl Cellulose in a Drum Coater, Followed by Capsule Filling Using Automatic Capsule Filling Machine HPMCAS (AQOAT® AS LF) and Ethyl cellulose N7 were dissolved under stirring for about 30 minutes in a solvent mixture of Ethanol and water. Triethyl citrate was added to the mixture and stirred for another 15 minutes. This solution was used to coat the empty Kcaps® HPMC hard capsules (size #0) in a pre-locked state, using a drum coater (Neocota 5D).

TABLE 8

Formulation Example 4—Coating on Kcaps ® HPMC Size 0 capsules (Batch size 90 g i.e. 833 capsules)

| Material | Composition | Solid Composition Percentage |
| --- | --- | --- |
| HPMCAS (AQOAT ® AS LF) | 1.0 mg/cm² | 38.46% |
| Ethyl cellulose N7 | 1.0 mg/cm² | 38.46% |
| Triethyl citrate | 30% on ds* | 23.07% |
| Ethanol: Water (80:20) | q.s. to 7% w/w solids | n/a** |
| Solid content | 7% w/w | n/a** |
| Total solid weight gain | 2.60 mg/cm² | n/a** |

*Quantity based on dry polymer substance [%]
**not applicable

TABLE 9

Process Parameters for Example 4

| Parameter | Value |
| --- | --- |
| Machine | Neocota 5D |
| Batch size [g] | 90 |
| Nozzle bore [mm] | 0.8 |
| Internal tube diameter [mm] | 3.0 |
| Peristaltic pump | Flowtec |
| Atomizing pressure [bar] | 1.5 |
| Flat pattern pressure [bar] | 0.5 |
| Room temperature [° C.] | 21-24 |
| Room humidity [% r.h.] | 50-60 |
| Pan speed [rpm] | 11 |
| Product temperature [° C.] | 29-33 |
| Spray rate [g/min/kg] | 11-19 |

Encapsulation Parameters/Observations 568 mg of immediate release metoprolol pellets (40% active) were filled into the polymer coated pre-locked capsules using automatic capsule filling machine AFTLAB (ACG) with a pellets filling set up using standard format size 0 tooling for capsule opening, transport, filling and closing. The machine output was set to 5,000-5,400 cps/hour.

Capsules filled in the automatic capsule filling machine, were coated with 2.0 mg/cm² polymer weight gain corresponding with 2.6 mg/cm² solid weight gain.

Process Observations:
Sliding issues from the magazine, some capsules could not be filled into the die cavities.
For some capsules, cap and body could not be separated.
Denting on the capsule body was also observed in rejected capsules
Low yield of 65.2% could be achieved (34.8% capsules were rejected by the machine)

Film Preparation and Testing:
HPMCAS (AQOAT® AS LF), Ethyl cellulose N7 polymer (1:1) and triethyl citrate (30% based on dry polymer substance) were dissolved under stirring for about 24 hours in a solvent mixture of Ethanol and water (80:20) (9.0 g solid content, solid composition percentage HPMCAS:Ethyl cellulose:triethyl citrate [38.46%:38.46%:23.07%]). The polymer solution was poured onto a Polytetrafluoroethylen covered glass plate and dried for 4 days at 40° C. After drying the film was conditioned for 16 hours at 23° C. and 50% relative humidity. The resulting film thickness was approx. 250 μm. Elongation at break was determined according to DIN EN ISO 527-3:2019-02. An elongation at break value of 3.1% was obtained.

Conclusion

The poor film flexibility of the coating layer composition resulted in poor performance of the coated capsules on the automatic capsule filling machine with high rejection rate and damage of capsules Due to the high rejection rate and observed damages it is expected that the capsules do not fulfill the requirements of the US pharmacopeia (USP42-NF37) according to monograph <711> Dissolution of delayed release dosage forms acceptance table 3 and 4.

Example 5 (Comparative)—Coating of Pre-Locked Empty Capsules with Anionic Cellulose Polymer without a Plasticizer in a Drum Coater, Followed by Capsule Filling Using Automatic Capsule Filling Machine HPMCAS (AQOAT® AS LF) polymer was dissolved under stirring for about 45 minutes in a solvent mixture of Ethanol and water. This solution was used to coat the empty capsules in a pre-locked state, using a drum coater Neocota 5D.

TABLE 10

Formulation Example 5—Coating on Kcaps ® HPMC Size 0 capsules (Batch size 90 g i.e. 833 capsules)

| Material | Composition | % solids Composition |
| --- | --- | --- |
| HPMCAS (AQOAT ® AS LF) | 2.0 mg/cm² | 100% |
| Ethanol: Water (80:20) | q.s. to 7% w/w solids | |
| Solid content | 7% w/w | |
| Total solid weight gain | 2.0 mg/cm² | |

TABLE 11

Process Parameters for Example 5

| Parameter | Value |
| --- | --- |
| Machine | Neocota 5D |
| Batch size [g] | 90 |
| Nozzle bore [mm] | 0.8 |
| Internal tube diameter [mm] | 3.0 |

TABLE 11-continued

Process Parameters for Example 5

| Parameter | Value |
| --- | --- |
| Peristaltic pump | Flowtrietec |
| Atomizing pressure [bar] | 1.5 |
| Flat pattern pressure [bar] | 0.5 |
| Room temperature [° C.] | 20-25 |
| Room humidity [% r.h.] | 50-60 |
| Pan speed [rpm] | 11 |
| Product temperature [° C.] | 27-29 |
| Spray rate [g/min/kg] | 11-22 |

Process Observations:

The surface of coated capsules was not smooth, indicative of uneven film formation. Capsule surface did not show any sign of crack or film damage when capsules were pressed.

Preparation of Blend for Capsule Filling

The dye was co-sifted thru 100 mesh with lactose in ~1:1 ratio. The blend was mixed in a blender with lactose granules in multiple steps using geometric mixing method. The final blend was unloaded and used for capsule filling.

TABLE 12

Blend formulation for capsule filling (Example 5)

| Material | % w/w Composition |
| --- | --- |
| HydroxyNaphthol Blue | 1% |
| Lactose granules | 99% |

Encapsulation Parameters/Observations

A. Automatic capsule filling machine AFTLAB (ACG) was used with standard format size 0 tooling. The machine output was set to 5,000-5,400 cps/hour. Capsule filling operation was smooth, capsules body and caps were easily opened and fit well into the machine parts. About 250 mg blend was filled into each polymer coated capsule.

B. For comparison about 250 mg blend was filled into each polymer coated pre-locked capsule manually.

Dye Test

Method according to USP 42 manograph <701>: Six filled capsules were subjected to the disintegration test using 600 mL of 0.1N HCl for two hours, without sinkers according to European Pharmacopeia, chapter 2.9.1. Any change in color/appearance was noted. Following are the observations;

A. Within first hour of exposure, four out of six capsules show substantial leakage with appearance of specks in all. Within two hours, substantial leakage was observed followed by disintegration of capsules indicating failure of protection.

B. Some small specks of purple color observed within first hour, indicative of minor penetration of HCl in capsules. Within two hours, substantial leakage was observed followed by disintegration of capsules.

Film Preparation and Testing:

HPMCAS (AQOAT® AS LF) was dissolved under stirring for about 24 hours in a solvent mixture of Ethanol and water (80:20) (9.0 g solid content, solid composition percentage AQOAT® AS LF was 100%). The polymer solution was poured onto a Polytetrafluoroethylen covered glass plate and dried for 4 days at 40° C. After drying the film was conditioned for 16 hours at 23° C. and 50% relative humidity. The resulting film thickness was approx. 250 µm. Elongation at break was determined according to DIN EN ISO 527-3:2019-02. An elongation at break value of 3.2% was obtained.

Conclusion

The poor film flexibility of the coating layer composition resulted in coating layer film damage using the automatic capsule filling machine resulting in high failure rate of acid protection. Due to the negative disintegration results it is expected that the capsules do not fulfill the requirements of the US pharmacopeia (USP42-NF37) according to monograph <711> Dissolution of delayed release dosage forms acceptance table 3 and 4.

The invention claimed is:

1. A process for preparing a polymer coated hard-shell capsule, filled with a fill comprising a biologically active ingredient, the process comprising:
   providing the polymer coated hard-shell capsule, comprising a body and a cap, in a pre-locked state to a capsule filling machine,
   separating the body and the cap,
   filling the body with the fill comprising a biologically active ingredient, and
   rejoining the body and the cap in a final-locked state;
   wherein in a closed state the cap overlaps the body either in a pre-locked state or in a final-locked state,
   wherein a material of the body and the cap comprises an ethyl-, methyl- or propyl-ether of cellulose, starch, or pullulan,
   wherein the polymer coated hard-shell capsule comprises a coating layer that covers the polymer coated hard-shell capsule in the pre-locked state,
   wherein the coating layer comprises one or more anionic cellulose(s), ethyl cellulose, and/or one or more starches comprising at least 35% by weight of amylose,
   wherein the coating layer is present in an amount of about 1 to 5.8 mg/cm$^2$, and
   wherein a dried film with a thickness of 250 µm, corresponding to a composition of the coating layer, shows an elongation at break of about 15 to 500%.

2. The process according to claim 1, wherein the coating layer comprises the one or more anionic cellulose(s) and wherein the one or more anionic cellulose(s) are selected from the group consisting of carboxymethyl ethyl cellulose, a salt of carboxymethyl ethyl cellulose, cellulose acetate phthalate, cellulose acetate succinate, cellulose acetate trimellitate, hydroxypropyl methyl cellulose phthalate, hydroxypropyl methyl cellulose acetate succinate, and a mixture thereof.

3. The process according to claim 1, wherein the coating layer comprises the one or more starches comprising at least 35% by weight of amylose and wherein the one or more starches comprising at least 35% by weight of amylose is selected from corn starch, maize starch, pre-gelled starch, acetylated starch, and a combination thereof.

4. The process according to claim 3, wherein the one or more starches comprising at least 35% by weight of amylose comprises 40 to 80% by weight of amylose.

5. The process according to claim 1, wherein the one or more anionic cellulose(s), the ethyl cellulose, and/or the one or more starches comprising at least 35% by weight of amylose have glass transition temperatures $T_{gm}$ of 130° C. or less.

6. The process according to claim 1, wherein the material of the body and the cap comprises hydroxypropyl methyl cellulose.

7. The process according to claim 1, wherein the coating layer comprises
- 10 to 100% by weight of the one or more anionic cellulose(s), the ethyl cellulose, and/or the one or more starches comprising at least 35% by weight of amylose, and
- 90 to 0% by weight of pharmaceutical or nutraceutical excipients.

8. The process according to claim 7, wherein the pharmaceutical or nutraceutical excipients comprise one or more plasticizers and/or one or more detacking agents.

9. The process according to claim 8, wherein the one or more plasticizers is/are present and are selected from the group consisting of an alkyl citrate, a glycerol ester, an alkyl phthalate, an alkyl sebacate, a sucrose ester, a sorbitan ester, a glycerol, a propylene glycol, and a polyethylene glycol.

10. The process according to claim 8, wherein the one or more detacking agents is/are present and are selected from the group consisting of Ca-stearate, Mg-stearate, glycerol monostearate, and talc.

11. The process according to claim 1, wherein the coating layer comprises an emulsifier.

12. The process according to claim 1, wherein the coating layer comprises polysorbate 80.

13. The process according to claim 1, wherein the capsule filling machine is operated at a speed with an output of 1,000 or more filled and finally closed capsules per hour.

14. A hard-shell capsule, obtained by the process according to claim 1.

15. The process according to claim 1, wherein the coating layer comprises one or more anionic cellulose(s) and/or one or more starches comprising at least 35% by weight of amylose.

16. The process according to claim 2, the one or more anionic cellulose comprises hydroxypropyl methyl cellulose acetate succinate.

17. The process according to claim 16, wherein the material of the body and the cap comprises hydroxypropyl methyl cellulose.

18. The process according to claim 15, wherein the coating layer is present in an amount of about 2 to 5 mg/cm$^2$.

19. The process according to claim 3, wherein the material of the body and the cap comprises hydroxypropyl methyl cellulose.

20. The process according to claim 9, wherein the one or more plasticizers comprises triethyl citrate.

* * * * *